US00PP23993P2

(12) United States Plant Patent
Hartman

(10) Patent No.: US PP23,993 P2
(45) Date of Patent: Oct. 15, 2013

(54) ***CALADIUM* PLANT NAMED 'CELEBRATION'**

(50) Latin Name: *Caladium×hortulanum*
Varietal Denomination: Celebration

(76) Inventor: Robert Dale Hartman, Lake Placid, FL (US)

( * ) Notice: Subject to any disclaimer, the term of this patent is extended or adjusted under 35 U.S.C. 154(b) by 116 days.

(21) Appl. No.: 13/374,462

(22) Filed: Dec. 29, 2011

(51) Int. Cl.
*A01H 5/00* (2006.01)

(52) U.S. Cl.
USPC ..... Plt./373

(58) Field of Classification Search
USPC ..... Plt./373
See application file for complete search history.

*Primary Examiner* — June Hwu
(74) *Attorney, Agent, or Firm* — C. A. Whealy

(57) ABSTRACT

A new and distinct cultivar of *Caladium* plant named 'Celebration', characterized by its upright plant habit; intermediate to tall plant size; uniform plant habit; vigorous and dense growth habit; fancy-type leaves with dark red-colored venation, white-colored interveinal areas surrounded by dark green-colored borders; and good landscape performance.

4 Drawing Sheets

Botanical designation: *Caladium×hortulanum.*
Cultivar denomination: 'CELEBRATION'.

BACKGROUND OF THE INVENTION

The present invention relates to a new and distinct cultivar of *Caladium* plant, botanically known as *Caladium×hortulanum*, commercially referred to as a fancy leaf-type *Caladium* and hereinafter referred to by the name 'Celebration'.

The objective of the Inventor's breeding program is to create new *Caladium* plants that have uniform plant habit, exceptional container and garden performance and attractive foliage coloration.

The new *Caladium* plant originated from a cross-pollination made by the Inventor on Apr. 15, 2007, in Avon Park, Fla. of *Caladium×hortulanum* 'John Peed', not patented, as the female, or seed, parent with *Caladium×hortulanum* 'White Christmas', not patented, as the male, or pollen, parent. The new *Caladium* plant was discovered and selected by the Inventor as a single plant within the progeny of the stated cross-pollination in a controlled outdoor nursery environment in Zolfo Springs, Fla. on Sep. 15, 2008.

Asexual reproduction of the new *Caladium* plant by 'chipping' the tubers (cutting the tuber into segments each segment containing an axillary bud and tuber cortical tissue) in a controlled outdoor nursery environment in Lake Placid, Fla. since Apr. 15, 2009 has shown that the unique features of this new *Caladium* plant are stable and reproduced true to type in successive generations of asexual reproduction.

SUMMARY OF THE INVENTION

Plants of the new *Caladium* have not been observed under all possible environmental conditions and cultural practices. The phenotype may vary somewhat with variations in environmental conditions such as temperature and light intensity, without, however, any variance in genotype.

The following traits have been repeatedly observed and are determined to be the unique characteristics of 'Celebration'. These characteristics in combination distinguish 'Celebration' as a new and distinct *Caladium* plant:

1. Upright plant habit; intermediate to tall plant size.
2. Uniform plant habit.
3. Vigorous and dense growth habit.
4. Fancy-type leaves with dark red-colored venation, white-colored interveinal areas surrounded by dark green-colored borders.
5. Good landscape performance and tolerant to full sun conditions.

Plants of the new *Caladium* differ primarily from plants of the female parent, 'John Peed', in the following characteristics:

1. Plants of the new *Caladium* grow faster than plants of 'John Peed'.
2. Plants of the new *Caladium* and 'John Peed' differ in leaf coloration as leaves of plants of 'John Peed' have red-colored venation and interveinal areas surrounded by dark green-colored margins.
3. Plants of the new *Caladium* and 'John Peed' differ in leaf petiole coloration as plants of 'John Peed' have dark red-colored leaf petioles.

Plants of the new *Caladium* differ primarily from plants of the male parent, 'White Christmas', in leaf coloration as leaves of plants of 'White Christmas' have dark green-colored venation, white-colored interveinal areas and dark green-colored borders.

Plants of the new *Caladium* can be compared to plants of *Caladium* 'Candidum', not patented. In side-by-side comparisons conducted in Avon Park, Fla., plants of the new *Caladium* differed primarily from plants of 'Candidum' in the following characteristics:

1. Leaves of plants of the new *Caladium* were more undulate than leaves of plants of 'Candidum'.
2. Plants of the new *Caladium* and 'Candidum' differed in leaf coloration as leaves of plants of 'Candidum' had green-colored venation, variably white-colored interveinal areas and green-colored margins.

Plants of the new *Caladium* can also be compared to plants of 'Tapestry', not patented. In side-by-side comparisons conducted in Lake Placid, Fla., plants of the new *Caladium* differed primarily from plants of 'Tapestry' in the following characteristics:

1. Plants of the new *Caladium* grew faster than plants of 'Tapestry'.
2. Plants of the new *Caladium* and 'Tapestry' differed in leaf coloration as leaves of plants of 'Tapestry' had rose pink-colored venation, white and pink-colored interveinal areas surrounded by olive green-colored borders.

BRIEF DESCRIPTION OF THE PHOTOGRAPHS

The accompanying photographs illustrate the overall appearance of the new *Caladium* plant showing the colors as true as it is reasonably possible to obtain in colored reproductions of this type. Colors in the photographs may differ slightly from the color values cited in the detailed botanical description which accurately describe the colors of the new *Caladium* plant.

The photograph on the first sheet is a side perspective view of a typical plant of 'Celebration' grown in a 15-cm container in a shadehouse.

The photograph at the top of the second sheet is a side perspective view of typical plants of 'Celebration' grown in an outdoor nursery.

The photograph at the bottom of the second sheet is a close-up view of typical freshly-harvested tubers and roots of 'Celebration'.

The photograph at the top of the third sheet is a comparison view of typical plants of 'Celebration' grown in 15-cm containers, the plant on the left has not had its tuber de-eyed and the plant on the right has had its tuber de-eyed prior to planting.

The photograph at the bottom left of the third sheet is a close-up view of the rear surface of typical inflorescences of 'Celebration'.

The photograph at the bottom right of the third sheet is a close-up view of the front surface of a typical inflorescence of 'Celebration'.

The photograph at the top of the fourth sheet is a comparison view of typical potted plants of the female parent, 'John Peed' (left), 'Celebration' (center) and the male parent, 'White Christmas' (right).

The photograph at the bottom of the fourth sheet is a comparison view of typical potted plants of 'Candidum' (left), 'Celebration' (center) and 'Tapestry' (right).

DETAILED BOTANICAL DESCRIPTION

The aforementioned photographs and following observations and measurements describe plants grown during the spring in 15-cm containers in Avon Park, Fla. in a polypropylene-covered shadehouse (30% shade) and plants grown in ground beds in an outdoor nursery in Zolfo Springs, Fla. during the autumn. All plants were grown under environmental conditions and cultural practices which approximate those generally used in commercial shadehouse and outdoor nursery *Caladium* production. During the production of the plants, day temperatures ranged from about 29° C. to 33° C. (shadehouse) or 29° C. to 35° C. (outdoor nursery), night temperatures ranged from about 22° C. to 25° C. (shadehouse) or 23° C. to 26° C. (outdoor nursery) and light levels were about 8,000 foot-candles (shadehouse) or 10,000 to 12,000 foot-candles (outdoor nursery). Plants grown in the shadehouse were seven weeks old when the photographs and the detailed description were taken. Plants grown in the outdoor nursery were seven months old when the photographs and the detailed description were taken. In the following description, color references are made to The Royal Horticultural Society Colour Chart, 2001 Edition, except where general terms of ordinary dictionary significance are used.

Botanical classification: *Caladium×hortulanum* 'Celebration'.

Parentage:

*Female, or seed, parent.*—*Caladium×hortulanum* 'John Peed', not patented.

*Male, or pollen, parent.*—*Caladium×hortulanum* 'White Christmas', not patented.

Propagation:

*Type.*—By "chipping" the tubers.

*Time to initiate roots, summer.*—About seven to ten days at 32° C.

*Time to initiate roots, winter.*—About two to three weeks at 24° C.

*Tuber description* (*outdoor nursery-grown plants*).—Appearance: Multi-segmented; individual segments ovate to elliptic in shape. Height: About 2.7 cm. Diameter: About 3.7 cm. Texture: Thick and starchy; somewhat brittle. Color: Epidermis, freshly harvested, close to 199A, 199C to 199D; epidermis, dried tuber, close to 200A; interior, close to 11D; axillary buds, close to 37D and 170D. Root description: Thick, fleshy contractile roots; color, close to 155C. Rooting habit: Few lateral branches; moderately dense.

Plant description:

*Plant type.*—Herbaceous perennial; suitable as a potted plant in containers 15-cm to 25-cm and suitable as a landscape plant in shaded and full sunlight areas.

*Plant and growth habit.*—Upright plant habit; intermediate to tall plant size; inverted triangle; vigorous and dense growth habit; rapid growth rate; petioles and leaves arise from one or more growing points on tubers; petioles mostly upright and arching outwardly with development.

*Plant height, from soil level to top of foliar plane, shadehouse-grown potted plants.*—About 35 cm to 41.5 cm.

*Plant height, from soil level to top of inflorescences, shadehouse-grown potted plants.*—About 36 cm.

*Plant diameter or spread, shadehouse-grown potted plants.*—About 42 cm to 50 cm.

*Number of clumps per plant, shadehouse-grown potted plants.*—About two to three from de-eyed tubers.

*Cataphylls, shadehouse-grown potted plants.*—Length: About 6 cm to 11.5 cm. Width: About 1 cm to 1.5 cm. Shape: Deltoid. Apex: Obtuse to emarginate, or acute. Base: Sheathing the stem. Color, outer surface: Close to N170D streaked and tessellated with close to 200A to 200B and 147A; with development, color becoming closer to 200A stained with close to 187A. Color, inner surface: Close to 155C.

Foliage description:

*Length, shadehouse-grown potted plants.*—About 23 cm to 30 cm.

*Width, shadehouse-grown potted plants.*—About 14 cm to 19.5 cm.

*Shape.*—Ovate.

*Apex.*—Acuminate.

*Base.*—Sagittate, peltate.

*Margin.*—Entire; mostly flat with some broad undulations.

*Texture, upper surface.*—Smooth, glabrous.

*Texture, lower surface.*—Smooth, glabrous; glaucous.

*Venation pattern*.—Pinnate.

*Color, shadehouse-grown potted plants*.—Developing leaves, upper surface: Basal notch: Close to 187B. Area between basal notch and petiole attachment: Close to 187C. Midrib: Close to 59B. Primary venation: Close to 59B to 59C. Areas surrounding the primary venation: Darker green than 147A. Interveinal areas: Random sectors and spots, close to 146B, 147D and 155C. Borders: Darker green than 147A. Margins: Close to 187B. Developing leaves, lower surface: Basal notch: Close to 187B. Area between basal notch and petiole attachment: Close to 185C to 185D. Midrib: Close to 181B. Primary venation: Close to 148C tinged with close to 181D. Areas surrounding the primary venation: Close to 185C to 185D and/or 191A and 189A. Interveinal areas: Random sectors and spots, close to 147B, 147C, 191A, 194A to 194B and close to 155C. Borders: Close to 191A and 189A. Margins: Close to 187B. Fully expanded leaves, upper surface: Basal notch: Close to 187C to 187D. Area between basal notch and petiole attachment: Close to 187C to 187D. Midrib and primary venation: Close to 59A to 59B. Areas surrounding the primary venation: Darker green than 147A. Interveinal areas: Random sectors and spots, close to 146A to 146B, 155C and 63D. Borders: Darker green than 147A. Margins: Close to 187B. Fully expanded leaves, lower surface: Basal notch: Close to 187B. Area between basal notch and petiole attachment: Close to 187B. Petiole attachment: Close to 185D. Midrib: Close to 181D. Primary venation: Close to 148D tinged with close to 181D. Areas surrounding the primary venation: Close to 185D and/or 191A. Interveinal areas: Random sectors and spots, close to 147C, 191A, 191B, 155C and close to 65D. Borders: Close to 191A. Margins: Close to 187B.

*Petiole*.—Aspect: Mostly erect, slightly outwardly leaning with development; flexible. Length, shadehouse-grown potted plants: About 25 cm to 36 cm. Diameter, distal, shadehouse-grown potted plants: About 4 mm to 6 mm. Diameter, proximal, shadehouse-grown potted plants: About 8 mm to 11 mm. Color, shadehouse-grown potted plants: Close to 200A variably striped, streaked and tessellated with close to N170D tinged with close to 147A; below the leaf/petiole junction, close to N170D tinged with close to 147C. Wing length, shadehouse-grown potted plants: About 5 cm to 6.5 cm. Wing diameter, shadehouse-grown potted plants: About 8 mm to 10 mm. Wing color, shadehouse-grown potted plants, outer surface: Close to N170D, streaked and tessellated with close to 147A and 200A. Wing color, shadehouse-grown potted plants, inner surface: Close to N155C, outer surface colors and patterns visible.

Inflorescence description: Inflorescences observed on eleven-week old shadehouse-grown potted plants.

*Inflorescence arrangement*.—Upright hooded spathes surrounding a columnar spadix borne on a tall upright scape; spadix with sessile, simple female and male flowers separated into two zones; female flowers arranged on the lower one-third of the spadix; male flowers arranged on the upper two-thirds of the spadix; sterile flowers develop at junction of female and male flower zones; near this junction, the spathe constricts and surrounds and encloses the female flowers; spathe open and cupped around male flowers.

*Fragrance*.—Night fragrant; moderate jasmine-like fragrance with camphor-like note.

*Natural flowering season/longevity*: Plants of the new *Caladium* typically flower during the spring or early summer in central Florida; flowers develop about eleven weeks after growth commences; inflorescences last about three days before fading; inflorescences persistent.

*Spathe*.—Length: About 10 cm; open length, about 6.5 cm and closed length, about 3.5 cm. Width, distal: About 2.5 cm. Width, proximal: About 2.2 cm. Width, at constriction: About 1.5 cm. Shape: Ovate. Apex: Acuminate. Base: Tapering to the peduncle. Margin: Entire. Texture, upper and lower surfaces: Smooth, glabrous. Color, front surface: Upper two-thirds: Close to 155C faintly marbled with close to 145C to 145D; with development, color becoming closer to 199B. Lower one-third: Close to 148C; color does not change with development. Color, rear surface: Upper two-thirds: Close to 155C marbled with close to 145B to 145C. Lower one-third: Close to 147B and 146B.

*Spadix*.—Length: About 8.7 cm. Length, male flower zone: About 5 cm. Length, sterile flower zone: About 1.5 cm. Length, female flower zone: About 2.2 cm. Diameter, male flower zone: About 1.1 cm. Diameter, sterile flower zone: About 6 mm. Diameter, female flower zone: About 9 mm. Shape: Columnar. Apex: Acute. Base: Obtuse. Aspect: Upright. Color, mature, male zone: Close to 158D. Color, mature, sterile zone: Close to 158D. Color, mature, female zone: Close to 10C to 10D. Male flowers: Quantity per spadix: About 202. Shape: Obovate. Height: About 3 mm. Diameter: About 3 mm. Pollen amount: None observed. Female flowers: Quantity per spadix: About 167. Shape: Obovate. Height: About 3 mm. Diameter: About 2 mm. Stigma color: Close to 10C to 10D. Ovary color: Close to 155D.

*Scape*.—Length: About 26 cm. Diameter: About 6 mm. Strength: Sturdy; flexible. Aspect: Erect. Texture: Smooth, glabrous; glaucous. Color: Close to N170D tinged with close to 147C and variably streaked, stippled or striped with close to 147B tinged with close to 200B; just below spathe, close to 147C faintly streaked with close to N170D and 147B tinged with close to 200A.

*Seeds and fruits*.—Seed and fruit development have not been observed on plants of the new *Caladium*.

Disease & pest tolerance/resistance: Plants of the new *Caladium* have been observed to have above average tolerance to *Xanthomonas* Leaf Spot and have average tolerance to *Pythium* Root Rot. Plants of the new *Caladium* have not been observed to have resistance to pests and other pathogens common to *Caladium* plants.

Temperature tolerance: Plants of the new *Caladium* have been observed to be tolerant to temperatures ranging from about 7° C. to about 40° C. and suitable for USDA Hardiness Zones 8A to 11.

It is claimed:

1. A new and distinct *Caladium* plant named 'Celebration' as illustrated and described.

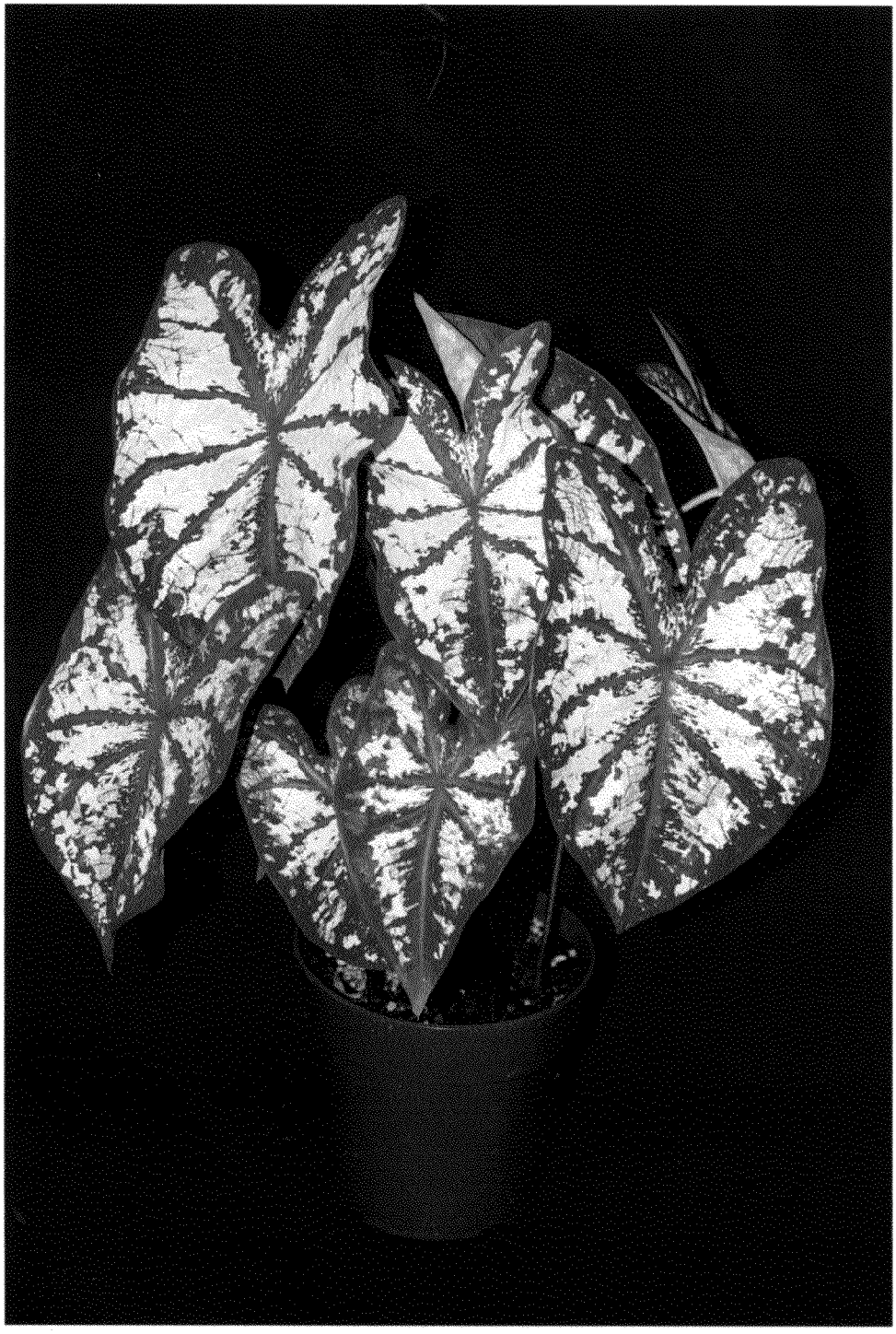

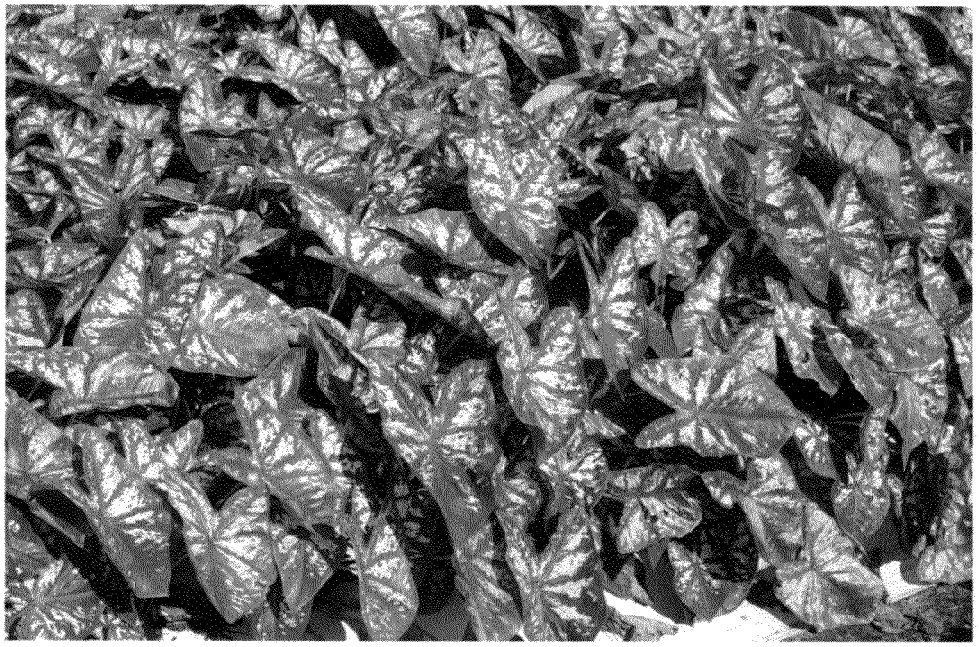
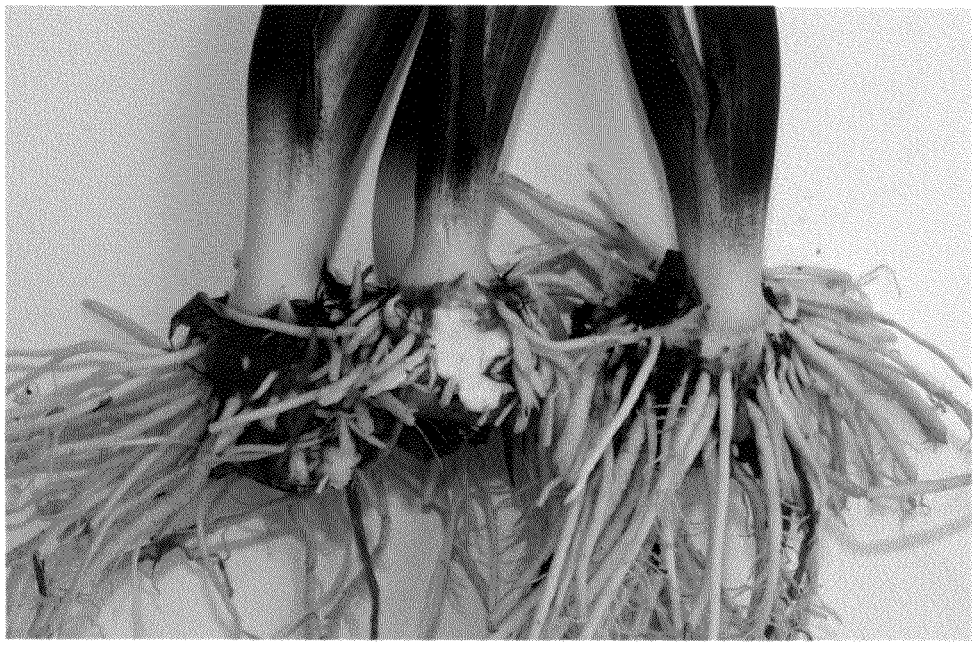

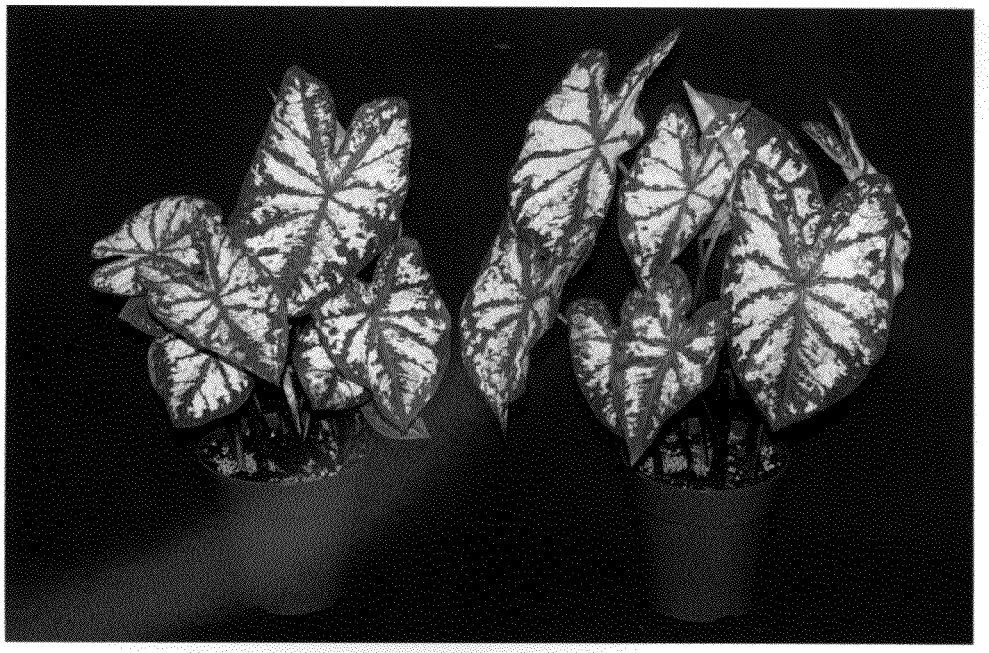
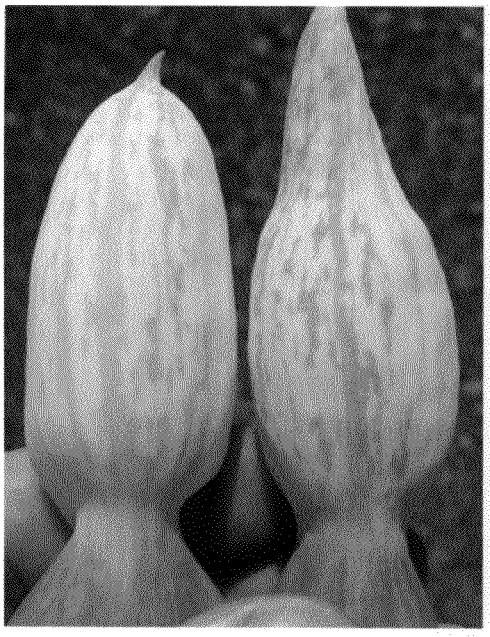
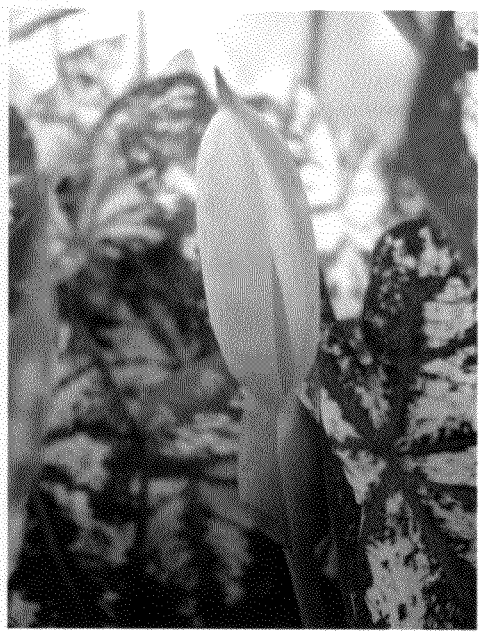

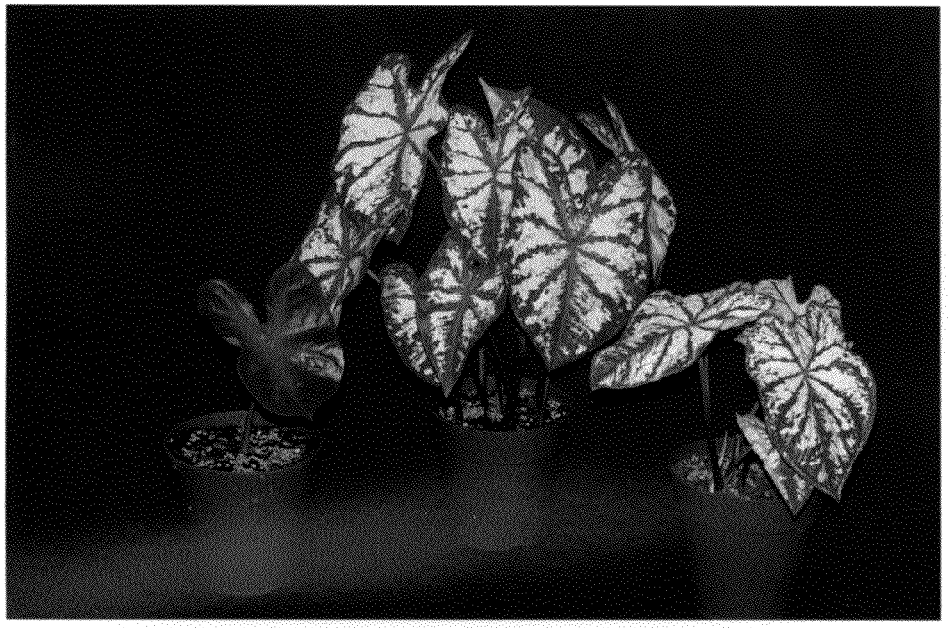
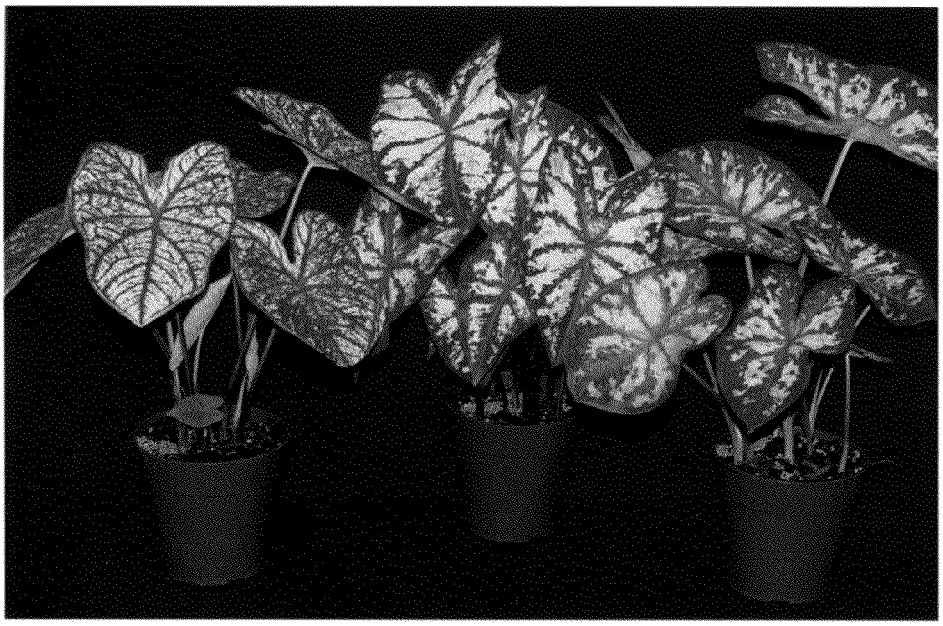

* * * * *